United States Patent
Kawamura et al.

(10) Patent No.: US 8,128,946 B2
(45) Date of Patent: *Mar. 6, 2012

(54) MEDICAL TAPE PREPARATION

(75) Inventors: Naohisa Kawamura, Kasukabe (JP); Hidenori Sawada, Kasukabe (JP); Takayuki Kobayashi, Saitama (JP)

(73) Assignee: Nipro Patch Co., Ltd., Saitama-ken (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/154,151

(22) Filed: Jun. 6, 2011

(65) Prior Publication Data

US 2011/0236440 A1  Sep. 29, 2011

Related U.S. Application Data

(63) Continuation of application No. 11/792,265, filed as application No. PCT/JP2005/022743 on Dec. 12, 2005, now Pat. No. 7,976,865.

(30) Foreign Application Priority Data

Dec. 15, 2004 (JP) .................... 2004-362331

(51) Int. Cl.
  *A61K 9/70* (2006.01)
  *C08L 15/00* (2006.01)
(52) U.S. Cl. .......... 424/400; 424/443; 523/111
(58) Field of Classification Search .......... None
See application file for complete search history.

(56) References Cited

U.S. PATENT DOCUMENTS

| | | | | |
|---|---|---|---|---|
| 4,759,983 A * | 7/1988 | Knutson et al. | 428/343 |
| 4,956,181 A * | 9/1990 | Bayer et al. | 424/448 |
| 5,185,212 A * | 2/1993 | Spada et al. | 428/483 |
| 5,254,348 A * | 10/1993 | Hoffmann et al. | 424/449 |
| 5,270,358 A | 12/1993 | Asmus | |
| 5,859,112 A * | 1/1999 | Overbeek et al. | 524/460 |
| 6,121,355 A | 9/2000 | Tsunemine et al. | 524/270 |
| 6,231,883 B1 | 5/2001 | Inosaka et al. | 424/443 |
| 7,939,100 B2 * | 5/2011 | Kawamura et al. | 424/448 |
| 7,976,865 B2 * | 7/2011 | Kawamura et al. | 424/443 |
| 2007/0154535 A1 | 7/2007 | Kawamura | 424/449 |

FOREIGN PATENT DOCUMENTS

| | | |
|---|---|---|
| EP | 0407667 | 1/1991 |
| EP | 0763583 A1 | 3/1997 |
| EP | 0 891 782 A2 | 7/1998 |
| JP | 06-108033 | 4/1994 |
| JP | 7057863 | 3/1995 |
| JP | 2000-026284 | 1/2000 |
| JP | 2000-026285 | 1/2000 |
| JP | 2000-038337 | 2/2000 |
| JP | 2000-044904 | 2/2000 |
| JP | 2001-1270839 | 10/2001 |
| JP | 2004-097730 | 4/2004 |
| JP | 2005-015353 | 1/2005 |
| JP | 2005-015537 | 1/2005 |
| WO | WO 86/06281 | 4/1986 |
| WO | WO 96/29373 | 9/1996 |
| WO | WO 2004/112760 | 12/2004 |

OTHER PUBLICATIONS

Eastman; http://www.eastman.com/Products/Pages/ProductHome.aspx?Product=71001078&list=Chemicals Waterborn Acrylic Emulsion Formulation Using Eastman Acetoacetoxyethyl Metacrylate, published Jul. 2003.

European Search Report dated Sep. 20, 2011 for European application No. 05814768.7.

Japanese Office Action dated Jan. 10, 2012 from Japanese Application No. 2006-548813.

* cited by examiner

*Primary Examiner* — Scott Long
*Assistant Examiner* — Sarah Alawadi
(74) *Attorney, Agent, or Firm* — Roylance, Abrams, Berdo & Goodman, L.L.P.

(57) ABSTRACT

A medical tape preparation which comprises a support and, superposed on one side thereof in the following order, a pressure-sensitive adhesive layer and a release liner. The pressure-sensitive adhesive layer can contain a large amount of an oleophilic oily matter. The tape preparation is excellent in adhesion, cohesiveness, and stability even when no crosslinking agent is used. The pressure-sensitive adhesive layer in the medical tape preparation comprises a blend of two tacky polymers, which are a tacky polymer (A) comprising a copolymer obtained from 2-acetoacetoxyethyl methacrylate and other vinyl monomer(s) as constituent ingredients and a tacky polymer (B) comprising a copolymer which is obtained from a $C_{4\text{-}10}$-alkyl(meth)acrylate and other vinyl monomer(s) as constituent ingredients and is different from the tacky polymer (A).

5 Claims, No Drawings

MEDICAL TAPE PREPARATION

CROSS-REFERENCE TO RELATED APPLICATIONS

This application is a Continuation application of U.S. patent application Ser. No. 11/792,265, filed on Jun. 4, 2007 now U.S. Pat. No. 7,976,865, which was the National Stage application of International Application No. PCT/JP05/22743, filed on Dec. 12, 2005, which claims benefit of, and priority to, Japanese Patent Application 2004-362331, filed on Dec. 15, 2004, all of which are herein incorporated by reference.

FIELD OF THE INVENTION

The present invention relates to a medical tape preparation employing a pressure-sensitive adhesive comprising a mixture of two copolymers, namely a copolymer whose constituent components are 2-acetoacetoxyethyl methacrylate ester and another vinyl monomer, and another acrylic-based copolymer, the medical tape preparation having excellent cohesion, adhesion and compatibility with lipophilic oils without the use of an external crosslinking agent.

BACKGROUND OF THE INVENTION

A patent relating to a medical tape preparation employing a pressure-sensitive adhesive comprising a mixture of two different pressure-sensitive adhesives is known (see Patent document 1), which is a tape preparation comprising a copolymer obtained by copolymerizing a carboxyl or hydroxyl group-containing monomer and a (meth)acrylic acid ester, and a copolymer obtained by copolymerizing a nitrogen-containing monomer with no salt structure on the side chains and a (meth)acrylic acid ester, which are crosslinked using an external crosslinking agent, but the copolymers used differ from those in the medical tape preparation of the invention and an external crosslinking agent is also not used for crosslinking according to the invention.

A patent relating to a medical patch employing a methacrylic-based polymer or vinyl acetate-based polymer and a copolymer obtained by copolymerizing a portion of the polymer component with a perfluoroalkyl(meth)acrylate ester is also known (see Patent document 2). However, the medical patch has different adhesion on the front and back sides of the pressure-sensitive adhesive, with essentially no adhesion on either the front or back, and it therefore differs substantially from the medical tape preparation of the invention.

Adhesives comprising a copolymer including 2-acetoacetoxyethyl methacrylate ester are also known (see Patent documents 3 and 4). However, these adhesives are used as coatings or adhesives and not as medical tape preparations. Moreover, no medical tape preparation is known that employs a pressure-sensitive adhesive comprising a mixture of a pressure-sensitive adhesive composed of a copolymer containing 2-acetoacetoxyethyl methacrylate ester, with another acrylic-based pressure-sensitive adhesive.

[Patent document 1] JP 2000-44904 A
[Patent document 2] JP 2000-38337 A
[Patent document 3] JP 7-57863 B
[Patent document 4] JP 6-108033 A

DISCLOSURE OF THE INVENTION

Problems to be Solved by the Invention

Lipophilic oil plasticizers are sometimes added to medical tape preparations in order to increase percutaneous absorption of percutaneous absorbable drugs, alleviate irritation to the skin or improve comfort during use, but the compatibility with conventional acrylic-based pressure-sensitive adhesives has been poor and the oil has separated from the pressure-sensitive adhesive layer during storage, thus limiting the amounts of lipophilic oils in plasticizers, drug solubilizers, percutaneous absorption accelerators and the like. In order to solve this problem, it has been attempted to crosslink acrylic-based pressure-sensitive adhesives using external crosslinking agents such as polyisocyanates, but this has led to problems such as excessively strong or insufficient cohesion and adhesion of the pressure-sensitive adhesives, or irritation to skin due to the use of the external crosslinking agents, and therefore a medical tape preparation with excellent cohesion and adhesion, as well as good compatibility between the pressure-sensitive adhesive layer and lipophilic oil, has been desired.

Means for Solving the Problems

As a result of much diligent research directed toward solving the problems stated above, the present inventors have discovered that a medical tape preparation with excellent cohesion and adhesion can be obtained, while satisfactorily maintaining compatibility with lipophilic oil substances, by producing a tape preparation using a mixture of a pressure-sensitive adhesive polymer comprising 2-acetoacetoxyethyl methacrylate ester as a constituent component, produced by copolymerizing 2-acetoacetoxyethyl methacrylate ester and another vinyl monomer, with an acrylic-based pressure-sensitive adhesive whose main constituent monomer is an alkyl (meth)acrylate ester.

Specifically, the medical tape preparation of the invention is a tape preparation having a pressure-sensitive adhesive layer and a release liner laminated in that order on one side of a support, the tape preparation being characterized in that the pressure-sensitive adhesive of the pressure-sensitive adhesive layer is a mixture of two different pressure-sensitive adhesives: (A) a pressure-sensitive adhesive polymer A comprising a copolymer whose constituent components are 2-acetoacetoxyethyl methacrylate ester and another vinyl monomer, and (B) a pressure-sensitive adhesive polymer B comprising a copolymer different from pressure-sensitive adhesive polymer A, whose constituent components are an alkyl(meth)acrylate ester with a $C_{4-10}$ alkyl group and another vinyl monomer.

The medical tape preparation of the invention also preferably contains a lipophilic oil such as isopropyl myristate in the pressure-sensitive adhesive layer as a plasticizer, and a percutaneous absorbable drug may also be included in the pressure-sensitive adhesive layer.

Effect of the Invention

The medical tape preparation of the invention is characterized in that the pressure-sensitive adhesive of the pressure-sensitive adhesive layer is a mixture of two different pressure-sensitive adhesives: a pressure-sensitive adhesive polymer A comprising a copolymer whose constituent components are 2-acetoacetoxyethyl methacrylate ester and another vinyl monomer, and a pressure-sensitive adhesive polymer B comprising a copolymer different from pressure-sensitive adhesive polymer A, whose constituent components are an alkyl (meth)acrylate ester with a $C_{4-10}$ alkyl group and another vinyl monomer. This will improve the cohesion, adhesion and long-term stability over medical tape preparations employing conventional acrylic-based pressure-sensitive adhesives.

It was also discovered that by using a pressure-sensitive adhesive comprising a blend of two different pressure-sensitive adhesive polymers according to the invention, it is possible to vastly improve the solubility of the lipophilic oil plasticizer and produce excellent compatibility between the pressure-sensitive adhesive and the lipophilic oil plasticizer.

Since the medical tape preparation of the invention has excellent compatibility with lipophilic oils, it is possible to add large amounts of oils such as plasticizers without crosslinking with an external crosslinking agent, and because no external crosslinking agents, such as polyisocyanate compounds, are used, the medical tape preparation of the invention exhibits excellent stability without irritation to skin.

The medical tape preparation of the invention may be used as a percutaneous absorption preparation containing a percutaneous absorbable drug, or as a medical material containing no drug, such as a taping material.

BEST MODE FOR CARRYING OUT THE INVENTION

The medical tape preparation of the invention is a medical tape preparation having a structure with a pressure-sensitive adhesive layer and a release liner laminated in that order on one side of a support.

The pressure-sensitive adhesive polymer A as component (A) in the pressure-sensitive adhesive layer of the invention is preferably a copolymer, whose constituent components are 2-acetoacetoxyethyl methacrylate ester and another vinyl monomer, dissolved or dispersed in a solvent that volatilizes upon hot drying during production of the medical tape preparation.

The content of the 2-acetoacetoxyethyl methacrylate ester in the pressure-sensitive adhesive polymer A used in the medical tape preparation of the invention is preferably 1 wt %-50 wt %, more preferably 10 wt %-50 wt % and even more preferably 10 wt %-45 wt % with respect to the total copolymer weight of the pressure-sensitive adhesive polymer A. If the content is less than 1 wt % the effect of the invention will be insufficient, and if it is greater than 50 wt % the adhesion will be undesirably inferior.

The other vinyl monomer to be copolymerized with the 2-acetoacetoxyethyl methacrylate ester may be any one that copolymerizes with 2-acetoacetoxyethyl methacrylate ester, and there may be used one or more selected from among, for example, alkyl(meth)acrylate esters with $C_{4-10}$ alkyl groups such as butyl(meth)acrylate, hexyl(meth)acrylate, 2-ethylhexyl(meth)acrylate ester and octyl(meth)acrylate ester as one of the vinyl monomers, and additionally methyl methacrylate, diacetoneacrylamide, tetraethyleneglycol di(meth)acrylate, hexaethyleneglycol di(meth)acrylate, 2-hydroxyethyl(meth)acrylate ester or the like.

Most preferred as pressure-sensitive adhesive polymer A are copolymers obtained by copolymerizing 2-acetoacetoxyethyl methacrylate ester, 2-ethylhexyl acrylate ester, diacetoneacrylamide, methyl methacrylate and tetraethyleneglycol dimethacrylate.

The pressure-sensitive adhesive polymer A may be produced by a copolymer production process employed for acrylic-based pressure-sensitive adhesives. An example thereof will now be explained. Monomers that copolymerize in solvents that volatilize upon heat drying during production of tape preparations, such as toluene and ethyl acetate, are copolymerized using a polymerization initiator such as benzoyl peroxide.

The pressure-sensitive adhesive polymer B as component (B) in the pressure-sensitive adhesive layer of the invention is an acrylic-based pressure-sensitive adhesive polymer composed of a copolymer obtained by copolymerizing an alkyl (meth)acrylate ester with a $C_{4-10}$ alkyl group and another vinyl monomer, and unlike pressure-sensitive adhesive polymer A, it does not contain 2-acetoacetoxyethyl methacrylate ester as a constituent component.

As alkyl(meth)acrylate esters with $C_{4-10}$ alkyl groups there may be mentioned butyl(meth)acrylate, hexyl(meth)acrylate, 2-ethylhexyl(meth)acrylate ester and octyl(meth)acrylate, of which any one or more may be selected as appropriate. The content of the alkyl(meth)acrylate ester with a $C_{4-10}$ alkyl group is preferably at least 40 wt % with respect to the total copolymer weight.

The other vinyl monomer as the constituent monomer of pressure-sensitive adhesive polymer B may be any ones that copolymerize with the alkyl(meth)acrylate ester with a $C_{4-10}$ alkyl group, and as examples there may be mentioned methyl methacrylate, diacetoneacrylamide, 2-hydroxyethyl(meth)acrylate ester, N-vinyl-2-pyrrolidone, vinyl acetate and the like, preferably with the use of one or more vinyl monomers as appropriate.

Preferred copolymers for pressure-sensitive adhesive polymer B include copolymers of 2-ethylhexyl methacrylate ester, butyl acrylate and methyl methacrylate with diacetoneacrylamide, copolymers of 2-ethylhexyl acrylate ester and butyl acrylate with methyl acrylate, copolymers of 2-ethylhexyl acrylate ester and 2-hydroxyethyl acrylate ester with vinyl acetate and copolymers of butyl acrylate and 2-ethylhexyl acrylate ester with diacetoneamide, and these copolymers are used in a form dissolved or dispersed in a solvent that volatilizes during production of the medical tape preparation, and can be produced in the same manner as in the production process for the copolymer of pressure-sensitive adhesive polymer A. The pressure-sensitive adhesive polymer B used may be a commercially available acrylic-based pressure-sensitive adhesive having the aforementioned constituent components, such as NISSETSU PE300 (trade name of Nippon Carbide Industries Co., Inc., copolymer of 2-ethylhexyl acrylate ester, 2-hydroxyethyl acrylate ester and vinyl acetate in a proportion of 17:2:1).

The blending proportion of pressure-sensitive adhesive polymer A and pressure-sensitive adhesive polymer B is preferably 1:9-4:1. Outside of this range, it may not be possible to achieve suitable cohesion and adhesion. By using pressure-sensitive adhesive polymer A and pressure-sensitive adhesive polymer B in combination, the pressure-sensitive adhesive force is improved over pressure-sensitive adhesive polymer A alone, thereby allowing long-term stable use.

In some cases, there may be added to the pressure-sensitive adhesive layer of the medical tape preparation of the invention, a lipophilic oil substance as a plasticizer to increase the plasticity of the pressure-sensitive adhesive, or as a percutaneous absorbable drug solubilizer or percutaneous absorption accelerator. There are no particular restrictions on lipophilic oil plasticizers, and as examples there may be mentioned fatty acid esters such as isopropyl myristate, ethyl laurate, isopropyl palmitate, diethyl sebacate and diisopropyl adipate, glycerin esters such as medium chain fatty acid glyceride, or castor oil and the like, among which any one or combination of two or more may be used. The content will differ depending on the purpose for which the medical tape preparation is to be used, but satisfactory compatibility can be achieved at up to 40 wt % of the total weight of the pressure-sensitive adhesive layer.

There are also no particular restrictions on drugs to be included in the medical tape preparation of the invention, and any one or combination of two or more percutaneous absorbable drugs or local external drugs may be used. As examples of drugs there may be mentioned steroid hormones, nonsteroidal analgesic anti-inflammatory drugs, tranquilizers, antihypertensive agents, ischemic heart disease therapeutic agents, antihistamines, anti-asthmatic drugs, antiparkinsonism agents, cerebral circulation activators, antiemetic drugs, antidepressant drugs, antidementia drugs, Sjogren's syndrome therapeutic agents, antiarrhythmic drugs, anticoagulants, gout suppressants, antifungal drugs, narcotic analgesics, β-blockers, β1 agonists, β2 agonists, antitumor drugs, diuretic drugs, antithrombotic drugs, histamine $H_1$ receptor antagonists, histamine $H_2$ antagonists, antiallergic drugs, serotonin antagonists, hypocholesteremic drugs, local anesthetics, smoking cessation aids, and the like.

As drug solubilizers there may be used any non-skin irritating solvents that can dissolve the drug used, and specifically there may be used lower alcohols such as ethanol, propanol and isopropanol, medium-chain alcohols such as hexanol and octanol, polyhydric alcohols such as glycerin, ethylene glycol and diethylene glycol, higher fatty acid esters, polyvinyl alcohol, N-methyl-2-pyrrolidone, crotamiton and the like, any of which solvents may be used alone or in combinations of two or more as drug solubilizers, with no limitations to these cited solvents.

As drug percutaneous absorption accelerators there may be used fatty acid esters such as isopropyl myristate, isopropyl palmitate and diethyl adipate, fatty acid polyhydric alcohol esters such as caprylic acid monoglyceride, caprylic acid triglyceride and sorbitan fatty acid esters, and terpenes such as 1-menthol, peppermint oil and limonene, which are commonly used for medical tape preparations.

The pressure-sensitive adhesive layer of the medical tape preparation of the invention may also contain, in addition to the aforementioned plasticizers, drug solubilizers and percutaneous absorption accelerators used as lipophilic oils, also other excipients, tackifiers and the like as necessary.

As examples of other excipients there may be mentioned silicon compounds such as silicic anhydride and light silicic anhydride, cellulose derivatives such as ethylcellulose, methylcellulose, carboxymethylcellulose sodium, hydroxypropylcellulose and hydroxypropylmethyl cellulose, water-soluble polymers such as polyvinyl alcohol, antioxidants such as dibutylhydroxytoluene, powders such as kaolin and titanium oxide, and other aromas, coloring agents and the like, which may be added in medically acceptable ranges.

There are no particular restrictions on tackifiers that may be suitably used, and they include alicyclic saturated hydrocarbon resins (synthetic petroleum resins), rosin ester derivatives, terpene-based resins, phenol-based resins and the like. As examples of alicyclic saturated hydrocarbon resins there may be mentioned ARKON P-100 (trade name of Arakawa Chemical Industries, Ltd.), and similar resins. As examples of rosin ester derivatives there may be mentioned ESTER GUM H (trade name of Arakawa Chemical Industries, Ltd.), KE-311 (trade name of Arakawa Chemical Industries, Ltd.), KE-100 (trade name of Arakawa Chemical Industries, Ltd.) and the like. As examples of terpene-based resins there may be mentioned YS RESIN (trade name of Yasuhara Chemical Co., Ltd.) and the like. These tackifiers may be used alone or in combinations of two or more. There are no particular restrictions on the amount of tackifier used, but preferably it is added at 1-35 wt % with respect to the total weight of the pressure-sensitive adhesive layer.

The support used in the medical tape preparation of the invention may be any support known to be usable for medical tape preparations, and depending on the purpose of use it may be a fabric such as an elastic or non-elastic woven fabric, nonwoven fabric, cloth or knit made of polyethylene, polypropylene, polyester or the like, a plastic film made of polyethylene, polypropylene, polyester, ethylene-vinyl acetate copolymer, vinyl chloride or the like, or a foam film such as urethane, polyurethane or the like, and any of these may be used alone or in laminated form.

The release liner used in the medical tape preparation of the invention protects the pressure-sensitive adhesive layer up until the medical tape preparation is used, and it is released at the time of use. Any release liner employed for known medical tape preparations may be used, such as a thin film of polyester, polyethylene, polypropylene, ethylene-vinyl acetate copolymer resin, polyurethane or metal foil, or a laminated film comprising a combination of such materials, a surface silicon-treated film that bonds to the pressure-sensitive adhesive layer, or a film having vapor of a metal such as aluminum deposited on the film surface.

The medical tape preparation of the invention can be produced by the same production processes used for known tape preparations that employ acrylic-based pressure-sensitive adhesive on pressure-sensitive adhesive layers. An example of such a process is explained below. Pressure-sensitive adhesive polymer A and pressure-sensitive adhesive polymer B are blended, if necessary with uniform admixture of a plasticizer, drug and other additives, and the mixture is evenly applied onto a support to the desired thickness. After application, the coating is heat dried to form a pressure-sensitive adhesive layer. The release liner is used to cover the coating prior to cutting to the desired size to produce a medical tape preparation. Alternatively, the pressure-sensitive adhesive layer may be spread onto the release liner beforehand and then the support covered with it.

The copolymer used for the invention, comprising as a constituent component 2-acetoacetoxyethyl methacrylate ester having acetoacetyl groups, undergoes self-crosslinking of its acetoacetyl groups as the solvent transpires in the heat drying step for production of the medical tape preparation, thus forming a network structure which is able to hold large amounts of oily substances such as plasticizers, percutaneous absorbable drug solubilizers, percutaneous absorption accelerators and the like. It can therefore hold a large amount of a percutaneous absorbable drug, to permit supply over an extended period. Also, since the pressure-sensitive adhesive of the invention does not require the use of crosslinking agents such as polyamines, isocyanate compounds and polyvalent metal chelates, their toxicity is not a concern and the adhesive does not produce skin irritation. In addition, since the cohesion and adhesion are long-lasting even with prolonged use, the stability is excellent.

EXAMPLES

A pressure-sensitive adhesive used in a medical tape preparation of the invention will now be explained in detail through the following examples, with the understanding that the invention is not limited only to the examples.

The following production processes for pressure-sensitive adhesives 1-5 are for pressure-sensitive adhesive polymer A and pressure-sensitive adhesive polymer B used in tape preparations of the invention.

Production of Pressure-Sensitive Adhesive 1

In a 2 liter four-necked flask equipped with a Dimroth condenser, thermometer, nitrogen gas blowing tube and stirring blade there were charged 157.5 g of 2-ethylhexyl acrylate ester, 35 g of 2-acetoacetoxyethyl methacrylate ester, 80.5 g of diacetoneacrylamide, 76 g of methyl methacrylate and 1.3 g of tetraethyleneglycol dimethacrylate, and then 525 g of ethyl acetate was added as a solvent and the components were dissolved to uniformity. The solution was heated to 75° C. while blowing in nitrogen gas at a flow rate of 100 ml/min. After maintaining a temperature of 75° C. for 30 minutes, 0.21 g of benzoyl peroxide dissolved in 5 g of ethyl acetate was added as a polymerization initiator and the external temperature was adjusted to 85° C. At 3, 5 and 7 hours after loading the initiator, there was loaded 100 g of toluene each time for a total of 300 g. During polymerization, nitrogen gas was continuously blown in at a flow rate of 100 ml/min. At 12 hours after the final loading of toluene, 0.35 g of benzoyl peroxide was loaded as additional catalyst and then the external temperature was set to 95° C. for 12 hours of heat treatment followed by cooling to obtain pressure-sensitive adhesive 1.

Physical Properties of Pressure-Sensitive Adhesive 1 Solution

Solution viscosity (measured by Brookfield viscometer): 30,000 mPas

Solid content (treatment at 150° C., 1 hour): 28.5%

Production of Pressure-Sensitive Adhesives 2, 3

Pressure-sensitive adhesive 2 and pressure-sensitive adhesive 3 were produced by the same process described for production of pressure-sensitive adhesive 1.

Production of Pressure-Sensitive Adhesives 4, 5

Pressure-sensitive adhesive 4 and pressure-sensitive adhesive 5 comprising pressure-sensitive adhesive polymer B containing no 2-acetoacetoxyethyl methacrylate ester were produced by the same process described for production of pressure-sensitive adhesive 1.

Pressure-Sensitive Adhesive 6

As pressure-sensitive adhesive 6 comprising pressure-sensitive adhesive polymer B containing no 2-acetoacetoxyethyl methacrylate ester, there was used the commercially available solvent-type acrylic-based pressure-sensitive adhesive NIS-SETSU PE300 (product of Nippon Carbide Industries Co., Inc.).

Compositions of Pressure-Sensitive Adhesives 1-6

The compositions of pressure-sensitive adhesives 1-6 are shown in Table 1.

Example 1

After weighing out 40 g of pressure-sensitive adhesive 1 in a screw cap bottle, 7.1 g of pressure-sensitive adhesive 6 was weighed out and stirred therewith in the bottle for over an hour. A coating tester (product of LTE-S, Wener Mathis AG) was used for coating and drying of the solution on a support (polyester film) to a dry coverage of about 140 mg/10 cm$^2$, and it was then covered with a release liner (silicon-treated polyester film) with the silicon surface in contact with the pressure-sensitive adhesive, to obtain a medical tape preparation for Example 1.

Example 2

There were weighed out into a screw cap bottle 40 g of pressure-sensitive adhesive 1, 7.1 g of pressure-sensitive adhesive 6 and 3.6 g of isopropyl myristate, and the mixture was stirred in the bottle for over an hour. A coating tester (product of LTE-S, Wener Mathis AG) was used for coating and drying of the solution on a support (polyester film) to a dry coverage of about 140 mg/10 cm$^2$, and it was then covered with a release liner (silicon-treated polyester film) with the silicon surface in contact with the pressure-sensitive adhesive, to obtain a medical tape preparation for Example 2.

Examples 3-21 and Comparative Examples 1-5

Examples 3-21 and Comparative Examples 1-5 were produced by the same production processes used for Examples 1 and 2.

Composition of Medical Tape Preparations

The medical tape preparations of Examples 1-21 and the medical tape preparations of Comparative Examples 1-5 are shown in Table 2 below.

TABLE 1

Table 1: Compositions of pressure-sensitive adhesives 1-6

| Monomer composition | Pressure-sensitive adhesive polymer A | | | Pressure-sensitive adhesive polymer B | | |
|---|---|---|---|---|---|---|
| | Pressure-sensitive adhesive 1 | Pressure-sensitive adhesive 2 | Pressure-sensitive adhesive 3 | Pressure-sensitive adhesive 4 | Pressure-sensitive adhesive 5 | Pressure-sensitive adhesive 6 |
| AAEM | 10.0 | 20.0 | 45.0 | — | — | — |
| DAAM | 23.0 | 19.7 | 11.4 | 23.1 | — | — |
| MMA | 21.7 | 18.4 | 10.1 | 25.1 | 25.8 | — |
| 2EHA | 45.0 | 41.6 | 33.2 | 26.0 | 37.1 | 85.0 |
| TEGDMA | 0.3 | 0.3 | 0.3 | — | — | — |
| BA | — | — | — | 25.8 | 37.1 | — |
| 2HEA | — | — | — | — | — | 10.0 |
| VA | — | — | — | — | — | 5.0 |

The solvents for pressure-sensitive adhesives 1-6 were all mixtures of ethyl acetate and toluene. AAEM: 2-acetoacetoxyethyl methacrylate ester, DAAM: diacetone acrylamide, MMA: methyl methacrylate, 2EHA: 2-ethylhexyl acrylate ester, TEGDMA: tetraethyleneglycol dimethacrylate, BA: butyl acrylate, 2HEA: 2-hydroxyethyl acrylate ester, VA: vinyl acetate

TABLE 2

Table 2: Medical tape preparations

| Example | Pressure-sensitive adhesive polymer A | | Pressure-sensitive adhesive polymer B | | Oil substance* |
|---|---|---|---|---|---|
| 1 | Pressure-sensitive adhesive 1 | 80 | Pressure-sensitive adhesive 6 | 20 | — |
| 2 | Pressure-sensitive adhesive 1 | 64 | Pressure-sensitive adhesive 6 | 16 | IPM 20 |
| 3 | Pressure-sensitive adhesive 1 | 72 | Pressure-sensitive adhesive 6 | 18 | IPM 10 |
| 4 | Pressure-sensitive adhesive 1 | 56 | Pressure-sensitive adhesive 6 | 14 | IPM 30 |
| 5 | Pressure-sensitive adhesive 1 | 48 | Pressure-sensitive adhesive 6 | 12 | IPM 40 |
| 6 | Pressure-sensitive adhesive 1 | 64 | Pressure-sensitive adhesive 6 | 16 | DES 20 |
| 7 | Pressure-sensitive adhesive 1 | 64 | Pressure-sensitive adhesive 6 | 16 | DPA 20 |
| 8 | Pressure-sensitive adhesive 1 | 64 | Pressure-sensitive adhesive 6 | 16 | MFTG 20 |
| 9 | Pressure-sensitive adhesive 1 | 64 | Pressure-sensitive adhesive 6 | 16 | Castor oil 20 |
| 10 | Pressure-sensitive adhesive 2 | 70 | Pressure-sensitive adhesive 6 | 30 | — |
| 11 | Pressure-sensitive adhesive 2 | 56 | Pressure-sensitive adhesive 6 | 24 | IPM 20 |
| 12 | Pressure-sensitive adhesive 3 | 80 | Pressure-sensitive adhesive 6 | 20 | — |
| 13 | Pressure-sensitive adhesive 3 | 70 | Pressure-sensitive adhesive 6 | 30 | — |
| 14 | Pressure-sensitive adhesive 3 | 60 | Pressure-sensitive adhesive 6 | 40 | — |
| 15 | Pressure-sensitive adhesive 3 | 50 | Pressure-sensitive adhesive 6 | 50 | — |
| 16 | Pressure-sensitive adhesive 3 | 40 | Pressure-sensitive adhesive 6 | 40 | IPM 20 |
| 17 | Pressure-sensitive adhesive 3 | 40 | Pressure-sensitive adhesive 6 | 60 | — |
| 18 | Pressure-sensitive adhesive 3 | 30 | Pressure-sensitive adhesive 6 | 70 | — |
| 19 | Pressure-sensitive adhesive 3 | 20 | Pressure-sensitive adhesive 6 | 80 | — |
| 20 | Pressure-sensitive adhesive 3 | 10 | Pressure-sensitive adhesive 6 | 90 | — |
| 21 | Pressure-sensitive adhesive 3 | 40 | Pressure-sensitive adhesive 4 | 40 | IPM 20 |
| Comp. Ex. 1 | Pressure-sensitive adhesive 3 | 100 | — | | — |
| Comp. Ex. 2 | Pressure-sensitive adhesive 3 | 80 | — | | IPM 20 |
| Comp. Ex. 3 | — | | Pressure-sensitive adhesive 4 | 80 | IPM 20 |
| Comp. Ex. 4 | | | Pressure-sensitive adhesive 5 | 80 | IPM 20 |
| Comp. Ex. 5 | | | Pressure-sensitive adhesive 6 | 80 | IPM 20 |

*IPM: isopropyl myristate, DES: diethyl sebacate, DPA: diisopropyl adipate, MFTG: medium-chain fatty acid triglyceride

Example 22

There were weighed out into a screw cap bottle 40 g of pressure-sensitive adhesive 1, 7.1 g of pressure-sensitive adhesive 6 and 1.6 g of ketoprofen, and the mixture was stirred in the bottle for over an hour. A coating tester (product of LTE-S, Wener Mathis AG) was used for coating and drying of the solution on a support consisting of a polyester film to a dry coverage of about 140 mg/10 cm$^2$, and it was then covered with a silicon-treated polyester film release liner with the silicon surface in contact with the pressure-sensitive adhesive, to obtain a medical tape preparation for Example 22. The ketoprofen content of the obtained preparation was 10 wt %.

Example 23

There were weighed out into a screw cap bottle 38 g of pressure-sensitive adhesive 1, 6.8 g of pressure-sensitive adhesive 6, 3.8 g of isopropyl myristate and 2 g of ketoprofen, and the mixture was stirred in the bottle for over an hour. A coating tester (product of LTE-S, Wener Mathis AG) was used for coating and drying of the solution on a support consisting of a polyester film to a dry coverage of about 140 mg/10 cm$^2$, and it was then covered with a silicon-treated polyester film release liner with the silicon surface in contact with the pressure-sensitive adhesive, to obtain a medical tape preparation for Example 23. The ketoprofen content of the obtained preparation was 10 wt %.

Comparative Examples 6-9

For Comparative Example 6, the pressure-sensitive adhesive 6 and ketoprofen were weighed out into the screw cap bottle and the mixture was stirred in the bottle for over an hour, after which the same procedure was carried out as in Example 22 to obtain a medical tape preparation. For Comparative Example 7, isopropyl myristate was further added to obtain the medical tape preparation. For Comparative Examples 8 and 9, an isocyanate crosslinking agent was added in addition to the components for Comparative Examples 6 and 7, to obtain medical tape preparations.

Compositions of Medical Tape Preparations

The medical tape preparations of Examples 22-23 and Comparative Examples 6-9 are shown in Table 3.

Table 3

TABLE 3

Medical tape preparations

| Example | Pressure-sensitive adhesive 1 | Pressure-sensitive adhesive 6 | Crosslinking agent* | Drug | Plasticizer** |
|---|---|---|---|---|---|
| 22 | 70 | 20 | — | 10 | — |
| 23 | 56 | 14 | — | 10 | IPM 20 |
| Comp. Ex. 6 | — | 90 | — | 10 | — |
| Comp. Ex. 7 | — | 70 | — | 10 | IPM 20 |
| Comp. Ex. 8 | — | 89.9 | 0.1 | 10 | — |
| Comp. Ex. 9 | — | 69.9 | 0.1 | 10 | IPM 20 |

*Isocyanate crosslinking agent (CK101, Nippon Carbide Industries Co., Inc.)
**IPM: isopropyl myristate

Test Examples

The medical tape preparations of Examples 1-23 of the invention and Comparative Examples 1-9 were used to evaluate the pressure-sensitive adhesive properties by the following (organoleptic) test methods from the viewpoint of cohesion, adhesion and oil substance compatibility.

1) Cohesion Test

The release liner was peeled from the medical tape preparation, and the pressure-sensitive adhesive surface was touched with a finger and evaluated on the following scale.

Evaluation Scale

○: Cohesion roughly equivalent to that of commercially available indomethacin-containing tape preparation S and commercially available felbinac-containing tape preparation F comprising natural rubber latexes.

Δ: Cohesion roughly equivalent to that of commercially available ketoprofen-containing tape preparation M and commercially available flurbiprofen-containing tape preparation Y comprising styrene-isoprene-styrene copolymers.

x: Cohesion inferior to that of commercially available products.

–: Evaluation not possible due to excessively low cohesion (semi-solid state).

2) Adhesion Test

The release liner was peeled from the medical tape preparation, and the pressure-sensitive adhesive surface was touched with a finger and evaluated based on the following criteria.

Evaluation Scale

○: Adhesion roughly equivalent to that of commercially available ketoprofen-containing tape preparation M and commercially available flurbiprofen-containing tape preparation Y comprising styrene-isoprene-styrene copolymers.

Δ: Adhesion roughly equivalent to that of commercially available indomethacin-containing tape preparation S and commercially available felbinac-containing tape preparation F comprising natural rubber latexes.

x: Adhesion inferior to that of commercially available products.

–: Evaluation not possible due to excessively low cohesion (semi-solid state).

3) Evaluation of Oil Substance Compatibility

The release liner was peeled from the medical tape preparation, and the condition of any adhesion of liquid substances on the surface of the release liner was observed using an optical microscope and evaluated based on the following criteria.

Evaluation Scale

○: No liquid substances on release liner surface.

x: Liquid substances on release liner surface.

–: Evaluation not possible due to excessively low cohesion (semi-solid state).

/: Not evaluated since no oil substances were present.

Evaluation Results

The medical tape preparations of Examples 1-23 of the invention and Comparative Examples 1-9 were evaluated in terms of cohesion, adhesion and compatibility between the pressure-sensitive adhesive and oil substances. The results are shown in Table 4.

TABLE 4

Table 4: Cohesion, Adhesion and oil substance compatibility of medical tape preparations

| Example | Cohesion | Adhesion | Compatibility |
|---|---|---|---|
| 1 | ○ | ○ | / |
| 2 | ○ | ○ | ○ |
| 3 | ○ | ○ | ○ |
| 4 | ○ | ○ | ○ |
| 5 | Δ | ○ | ○ |
| 6 | ○ | ○ | ○ |
| 7 | ○ | ○ | ○ |
| 8 | ○ | ○ | ○ |
| 9 | ○ | ○ | ○ |
| 10 | ○ | ○ | / |
| 11 | ○ | ○ | ○ |
| 12 | ○ | Δ | / |
| 13 | ○ | ○ | / |
| 14 | ○ | ○ | / |
| 15 | ○ | ○ | / |
| 16 | ○ | ○ | ○ |
| 17 | ○ | ○ | / |
| 18 | ○ | ○ | / |
| 19 | ○ | ○ | / |
| 20 | ○ | ○ | / |
| 21 | ○ | ○ | ○ |
| 22 | ○ | ○ | / |
| 23 | ○ | ○ | ○ |
| Comp. Ex. 1 | ○ | x | / |
| Comp. Ex. 2 | ○ | x | x |
| Comp. Ex. 3 | x | — | — |
| Comp. Ex. 4 | x | — | — |
| Comp. Ex. 5 | x | — | — |
| Comp. Ex. 6 | x | — | / |
| Comp. Ex. 7 | x | — | — |
| Comp. Ex. 8 | x | — | / |
| Comp. Ex. 9 | x | — | — |

The medical tape preparations of Comparative Examples 1 and 2 had excellent cohesion but were unsatisfactory in terms of their adhesion and compatibility between oil substances and the pressure-sensitive adhesives, while the medical tape preparations of Comparative Examples 3-9 were inadequate in all of their properties. In contrast, the medical tape preparations of Examples 1-23 of the invention had excellent cohesion, adhesion and compatibility between oil substances and the pressure-sensitive adhesives, both without addition of a drug and with addition of a drug.

What is claimed is:

1. A medical tape preparation comprising a pressure-sensitive adhesive layer and a release liner laminated in that order on one side of a support, wherein the pressure-sensitive adhesive layer comprises a pressure-sensitive adhesive that is a mixture of two different pressure-sensitive adhesives:

(A) a pressure-sensitive adhesive polymer A comprising a copolymer whose constituent components comprise 2-acetoacetoxyethyl methacrylate ester and another vinyl monomer, and (B) a pressure-sensitive adhesive polymer B comprising a copolymer different from pressure-sensitive adhesive polymer A, whose constituent components comprise an alkyl (meth)acrylate ester with a $C_{4-10}$ alkyl group and another vinyl monomer, wherein the proportion of the pressure-sensitive adhesive polymer A and the pressure-sensitive adhesive polymer B is 1:9-4:1, and the content of the 2-acetoacetoxyethyl methacrylate ester in pressure-sensitive adhesive polymer A is 10 wt %- 45 wt % with respect to the total weight of the copolymer in pressure-sensitive adhesive polymer A.

2. The medical tape preparation according to claim 1, wherein:
   (A) the pressure-sensitive adhesive polymer A comprises 2-acetoacetoxyethyl methacrylate ester, and one or more vinyl monomer selected from:
   alkyl(meth)acrylate esters with $C_{4-10}$ alkyl groups,
   methyl methacrylate,
   diacetoneacrylamide,
   tetraethyleneglycol di(meth)acrylate,
   hexaethyleneglycol di(meth)acrylate, and
   2-hydroxyethyl(meth)acrylate ester,
   and
   (B) the pressure-sensitive adhesive polymer B comprises alkyl(meth)acrylate ester with a $C_{4-10}$ alkyl group and one or more vinyl monomer selected from:
   methyl methacrylate,
   diacetoneacrylamide,
   2-hydroxyethyl(meth)acrylate ester,
   N-vinyl-2-pyrrolidone, and
   vinyl acetate.

3. A medical tape preparation according to claim 1, wherein said pressure-sensitive adhesive layer further comprising a plasticizer comprising an oil component that is compatible with the pressure-sensitive adhesive composed of the mixture of the pressure-sensitive adhesive polymer A as component (A) and the pressure-sensitive adhesive polymer B as component (B).

4. A medical tape preparation according to claim 3, wherein said plasticizer is one or more oils selected from the group consisting of isopropyl myristate, diethyl sebacate, diisopropyl adipate, medium chain fatty acid triglyceride and castor oil.

5. A medical tape preparation according to claim 1, wherein the pressure-sensitive adhesive layer contains a percutaneous absorbable drug.

* * * * *